(12) United States Patent
Neumann et al.

(10) Patent No.: US 9,429,531 B2
(45) Date of Patent: Aug. 30, 2016

(54) THERMOANALYSIS DEVICE

(71) Applicant: Netzsch-Gerätebau GmbH, Selb (DE)

(72) Inventors: Georg Neumann, Schoenwald (DE);
Alexander Schindler, Leupoldsgruen (DE); Juergen Blumm, Selb (DE)

(73) Assignee: Netzsch-Gerätebau GmbH, Selb (DE)

( * ) Notice: Subject to any disclaimer, the term of this patent is extended or adjusted under 35 U.S.C. 154(b) by 506 days.

(21) Appl. No.: 13/917,382

(22) Filed: Jun. 13, 2013

(65) Prior Publication Data

US 2013/0336355 A1  Dec. 19, 2013

(30) Foreign Application Priority Data

Jun. 13, 2012  (DE) .................. 10 2012 105 101

(51) Int. Cl.
*G01N 25/00* (2006.01)
*G01N 25/20* (2006.01)
*G01J 5/02* (2006.01)

(52) U.S. Cl.
CPC .................. *G01N 25/00* (2013.01); *G01J 5/02* (2013.01); *G01N 25/20* (2013.01)

(58) Field of Classification Search
CPC combination set(s) only.
See application file for complete search history.

(56) References Cited

U.S. PATENT DOCUMENTS

| | | | | |
|---|---|---|---|---|
| 467,665 A * | 1/1892 | Chernin | ................. | A43D 69/04 227/97 |
| 804,299 A * | 11/1905 | Gijffels | .................... | A62C 2/16 160/298 |
| 4,914,297 A | 4/1990 | Wieboldt et al. | | |
| 6,518,572 B1 * | 2/2003 | Kishii | ..................... | G01N 21/35 250/339.08 |
| 2003/0185273 A1* | 10/2003 | Hollander | ................. | G01J 5/02 374/121 |
| 2005/0036146 A1* | 2/2005 | Braig | ..................... | G01N 21/03 356/436 |

FOREIGN PATENT DOCUMENTS

| | | |
|---|---|---|
| DE | 19934448 A1 | 8/2000 |
| DE | 10001382 A1 | 9/2000 |
| DE | 10052511 A1 | 5/2002 |

\* cited by examiner

*Primary Examiner* — Lisa Caputo
*Assistant Examiner* — Nasir U Ahmed
(74) *Attorney, Agent, or Firm* — Whitmyer IP Group LLC

(57) ABSTRACT

A device for thermal analysis. This device includes at least one thermoanalytical measurement device and at least one infrared spectrometer, wherein the infrared spectrometer is fully integrated into the thermoanalytical measurement device. The thermoanalytical measurement device and the at least one infrared spectrometer are connected to one another by a lift-swivel unit. The at least one infrared spectrometer is disposed above the thermoanalytical measurement device.

14 Claims, 5 Drawing Sheets

THERMOANALYSIS DEVICE

FIELD OF THE INVENTION

A device for thermal analysis is disclosed. This device comprises at least one thermoanalytical measurement device and at least one infrared spectrometer.

BACKGROUND OF THE INVENTION

Devices and methods for "thermoanalysis" are known from the prior art and have now become established worldwide, in particular for purposes of material characterisation. Polymers, pharmaceutical substances, textiles, metals, ceramics and other organic or inorganic materials, for example, can thus be analysed and characterised.

In "thermoanalysis" (or "thermal analysis"), a sample to be investigated is subjected by means of a temperature control device (e.g. electrical heating device) to a controlled temperature change, e.g. a pre-adjustable "temperature program". The sample may be heated, cooled or held at a constant temperature.

Complying as precisely as possible with the temperature program usually requires that the sample temperature is continuously detected, for example is measured with a temperature measuring sensor, so that a detection or measurement signal representative of the sample temperature can be used for a control (e.g. PID control) of the sample temperature.

Moreover, during the controlled change in the sample temperature, at least one (further) signal characteristic of a (further) property of the sample is continuously detected and recorded together with the course of the sample temperature.

Thermoanalysis thus enables the investigation and characterisation of temperature-related changes in properties of a sample material, including processes triggered thermally in the sample.

It is understood that the term "continuously" used here in connection with a detection (e.g. measurement) of signals also includes a quasi-continuous detection, for example one taking place at relatively small time intervals (e.g. periodically).

Thermoanalytical methods can be specified more precisely depending on which further signal or which further signals (apart from the sample temperature) are detected during the controlled change in the sample temperature. Such special methods of thermoanalysis are also known from the prior art and do not therefore require further explanation here. The following methods are mentioned solely by way of example: differential thermoanalysis (DTA), differential calorimetry (DSC) or dynamic differential calorimetry (DDK), thermogravimetry (TG) or thermogravimetric analysis (TGA) and thermomechanical analysis (TMA).

TG or a "simultaneous thermal analysis" (STA), i.e. a combination of TG and DSC or DDK, is often used for the characterisation of thermal vaporisation and decomposition effects. In a further development, apart from the detection of a loss of mass of the sample, an investigation of gases that are liberated by the sample can for example also take place. For the gas investigation, use can be made for example of Fourier transform infrared spectrometry (FTIR) or mass spectrometry (MS, for example using a quadrupole mass spectrometer).

The previously described measurement devices are generally characterised by a not inconsiderable size. The combination of two or more measurement devices and/or measurement methods is thus associated with a not inconsiderable requirement for space and equipment. The problem underlying the invention, therefore, is to create a compact measurement device, wherein an infrared spectrometer is efficiently and economically connected to a thermoanalytical measurement device.

In particular, the following publications are known from the prior art:

German patent application DE 100 52 511 A1 discloses a method and a device for evaluating chemical reaction processes. The described invention relates to a system for monitoring chemical reaction processes, in particular for detecting exothermic chemical reaction processes, and the use of such a system or a thermal radiation-sensitive sensor device, as well as a method for monitoring a plurality of chemical reaction mixtures. Furthermore, the disclosed invention relates to the area of combinatorial chemistry, in particular a method and a device for the monitoring and, if appropriate, control of exothermic reaction processes, preferably in so-called screening methods. The detection and evaluation of the measurement data preferably takes place by means of the sensor device and an associated evaluation device. Optionally, however, the evaluation can also take place in part or completely in the sensor device. The sensor device or its IR camera delivers measurement signals depending on the detected thermal radiation, said measurement signals being processed by the evaluation, in particular taking account of the temporal course or sequence. The processed signals, which for example represent the temporal course of the exothermicity or the temperature of the individual reaction mixtures, can preferably be displayed, printed out and/or outputted for further processing or storage, for example via a standardised interface or suchlike.

U.S. Pat. No. 4,914,297 shows an interface unit for a thermogravimetric analysis flow cell. The analysis flow cell comprises an elongated tubular cell body and an inlet and outlet made of glass for the flow of a gas. Furthermore, the device comprises a window element, which is permeable to infrared radiation, so that IR radiation can enter into and exit from the cell body. In addition, a mirror element is present for reflecting the IR radiation. The mirror element and the window element are mounted on the cell body in such a way that the overall unit can be quickly dismantled and reassembled.

Another German patent application, DE 100 01 382 A1, discloses an integral construction with a downstream opening section of a first furnace pipe, which is connected to a side face of a second cylindrical furnace pipe. The patent application also discloses a light transmission window, which is provided in the opening sections at the respective ends of a second furnace pipe, as well as a gas discharge section, which is disposed at least at one position in the side face of the second furnace pipe.

DE 199 34 448 A1 describes a method for performing differential thermoanalysis, which considerably reduces the equipment expenditure for the measurement by the fact that, compared to the previously known methods, the measurement and evaluation by means of only one measuring device is required, and which detects the heat of reaction alongside a signal type different from the heat of reaction. The invention is characterised in that a sample is heated/cooled according to a temperature program, during the heating/cooling the sample temperature is measured and stored, the mean heating rate beta is calculated from the stored values according to an equation and the difference between the stored values of the sample temperature and the temperature calculated from mean heating rate beta by means of an equation 2 is then determined.

SUMMARY OF THE INVENTION

The problem according to the invention is solved by a device comprising at least one thermoanalytical measurement device and at least one infrared spectrometer. Further advantageous embodiments can be found in the features of the sub-claims.

A device for thermal analysis is disclosed. This device comprises at least one thermoanalytical measurement device and at least one infrared spectrometer, wherein the infrared spectrometer forms a measurement system with the thermoanalytical measurement device. The thermoanalytical measurement device and the infrared spectrometer are connected via at least one lift-swivel unit, wherein the infrared spectrometer is disposed above the thermoanalytical measurement device.

The device for thermal analysis comprises a furnace for heating a sample which is introduced into the thermoanalytical measurement device. The infrared spectrometer is connected to the furnace via a coupling. The coupling is located between the furnace and the infrared spectrometer, so that it connects the furnace and the infrared spectrometer fixedly to one another. In a preferred embodiment, the coupling is connected to the furnace and to the infrared spectrometer by a threaded joint. By means of this threaded joint, it is possible to separate the furnace from the infrared spectrometer in order, for example, to use the thermoanalytical measurement device separately. This approach may be advisable in the case of samples whose gaseous pyrolysis products exhibit a high degree of contamination or could damage the infrared spectrometer.

In order to improve the measurement results of the device for thermal analysis and to avoid condensation in the coupling, the latter is heated. There is here also one of the advantages of the device for thermal analysis according to the invention compared with the devices known from the prior art. In the case of the known devices, use is made of transfer lines with a length of up to 2 meters. These transfer lines are expensive to heat and contain spaces in which gases can condense and/or deposits can arise. The subsequent measurement result of the infrared spectrometer may possibly be falsified by condensation and/or deposits. A replacement of the usual transfer lines, for example to measure a sensitive sample, is also much more expensive than the replacement of the coupling in the case of the device according to the invention. It is however not possible to completely dispensed with the coupling. The coupling is also used as a spacer between the furnace and the infrared spectrometer. If the infrared spectrometer were disposed directly above or directly on the furnace, the infrared spectrometer could become heated due to the hot exhaust air from the furnace. The heating would markedly influence the measurement accuracy of the infrared spectrometer. Furthermore, excessive heating of the infrared spectrometer can lead to destruction of the device.

The infrared spectrometer and the furnace can be raised and swiveled by means of the lift-swivel unit. The raising and swiveling is necessary in order to be able to put a new sample on the sample holder, which projects out of the thermoanalytical measurement device. In a preferred embodiment, the device is provided with a sample changer. The sample changer can be traversed by means of the lift-swivel unit to the location of the infrared spectrometer.

The lift-swivel unit is provided with at least one lifting device. The lifting device is a hydraulic, a mechanical or an electromechanical device. The lift-swivel unit can be used in a fully or partially automated manner. It is clear to the person skilled in the art that many possibilities are known from the prior art for raising and/or displacing measurement devices of different sizes. The aforementioned list does not therefore represent a conclusive limitation of the invention.

Furthermore, it is possible to provide the device for thermal analysis with a further measurement device in addition to the infrared spectrometer, wherein both measurement devices are connected via the lift-swivel unit to the thermoanalytical measurement device.

The thermoanalytical measurement device is a measurement device for differential thermal analysis or differential calorimetry, or more precisely for dynamic differential calorimetry, or for thermogravimetry, or more precisely for thermogravimetric analysis, or for simultaneous thermal analysis or thermomechanical analysis. The infrared spectrometer is a measurement device for Fourier transform infrared spectroscopy and/or for near-infrared spectroscopy.

Here too, it is clear to the person skilled in the art that a plurality of measurement devices can be connected and moved with one another by means of the at least one lift-swivel connection. It is also conceivable for measurement devices for the sole detection of temperatures to be disposed above the furnace. Depending on which products are heated in the furnace, it is also conceivable to provide the furnace via the coupling with a filter which keeps harmful gases out of the laboratory atmosphere.

The use of the device according to the invention could proceed as follows. The infrared spectrometer disposed above the thermoanalytical measurement device is raised together with a coupling and a furnace by means of a lift-swivel unit. It is then removed from its position above the sample holder of the thermoanalytical measurement device. During the removal of the infrared spectrometer, a sample changer is traversed into the original position of the infrared spectrometer. A sample from the sample changer is put onto a sample holder. If a sample from a previous measurement is already present on the sample holder, the latter is removed before the new sample is put on. The infrared spectrometer and the furnace are then traversed by means of the lift-swivel unit back over the thermoanalytical measurement device. Following the connection of the thermoanalytical measurement device and the infrared spectrometer, the sample is heated in the furnace. The sample is heated to temperatures from 400° to 1800° Celsius. This large temperature range is necessary, since samples from organic material as well as samples with a very high temperature resistance are investigated with the device. Samples with very high temperatures resistance can for example be ceramic materials. Outgassing of product constituents or pyrolysis, wherein gases and/or gaseous products are also liberated, occurs as a result of heating. The liberated gases and/or gaseous products are fed to the infrared spectrometer via the coupling. The chemical composition of the gas and/or the gaseous product is then determined in the infrared spectrometer.

Examples of embodiment of the invention and its advantages are explained in detail below with the aid of the appended figures. The size ratios of the individual elements with respect to one another in the figures do not always correspond to the actual size ratios, since some forms are represented simplified and other forms, for the sake of better clarity, magnified in relation to the other elements.

DETAILED DESCRIPTION OF THE INVENTION

Identical reference numbers are used for identical or identically acting elements of the invention. Furthermore, for the sake of greater clarity, only those reference numbers are represented in the individual figures that are required for the description of the respective figure. The represented embodiments merely represent examples of how the device for thermal analysis according to the invention can be embodied and do not represent a conclusive restriction.

Figure 1:
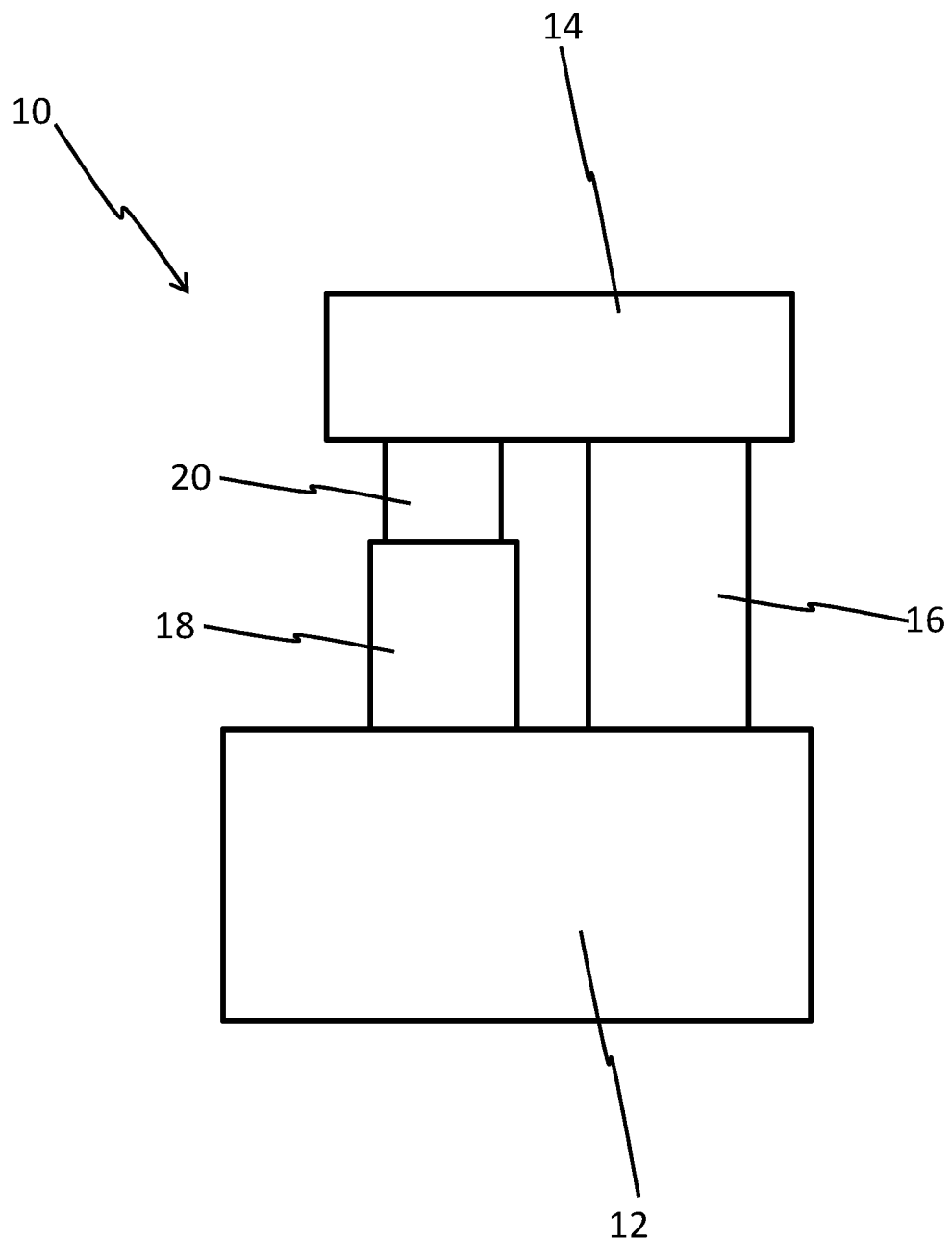
FIG. 1 a device according to the invention for thermal analysis.

FIG. 1 shows a device 10 for thermal analysis according to the invention. A thermoanalytical measurement device 12 is disposed in the lower region of device 10. Thermoanalytical measurement device 12 is connected to an infrared spectrometer 14 by means of a lift-swivel unit 16. Furnace 18, for heating samples, is connected fixedly to infrared spectrometer 14 by means of a coupling 20.

Figure 2:
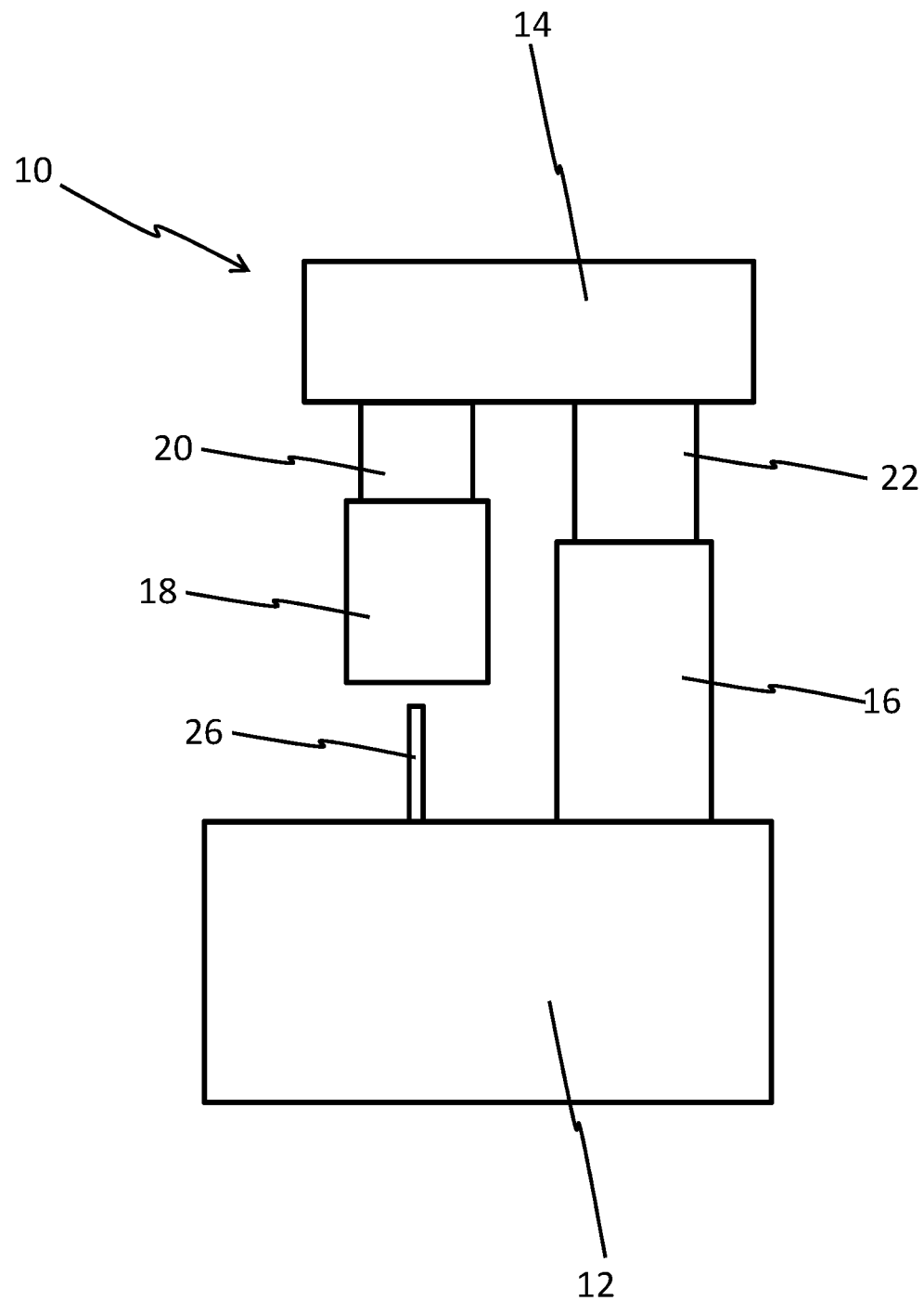
FIG. 2 shows a device according to the invention for thermal analysis in an opened state

FIG. 2 shows a device 10 for thermal analysis according to the invention in an opened state. The infrared spectrometer 14 has been raised by means of lift-swivel unit 16, so that furnace 18 is separated from thermoanalytical measurement device 12. Furnace 18 and infrared spectrometer 14 are also connected to one another via a coupling 20. The raising of the combination of furnace 18 and infrared spectrometer 14 takes place by means of a lifting device 22, which is located in lift-swivel unit 16. It is clear to the person skilled in the art that there are many embodiments for such lifting devices 22. Thus, for example, lifting device 22 can be a hydraulic, mechanical or electro-mechanical lifting device 22. Sample holder 26 is released by the lifting of furnace 18, so that new samples can be introduced into device 10.

Figure 3:
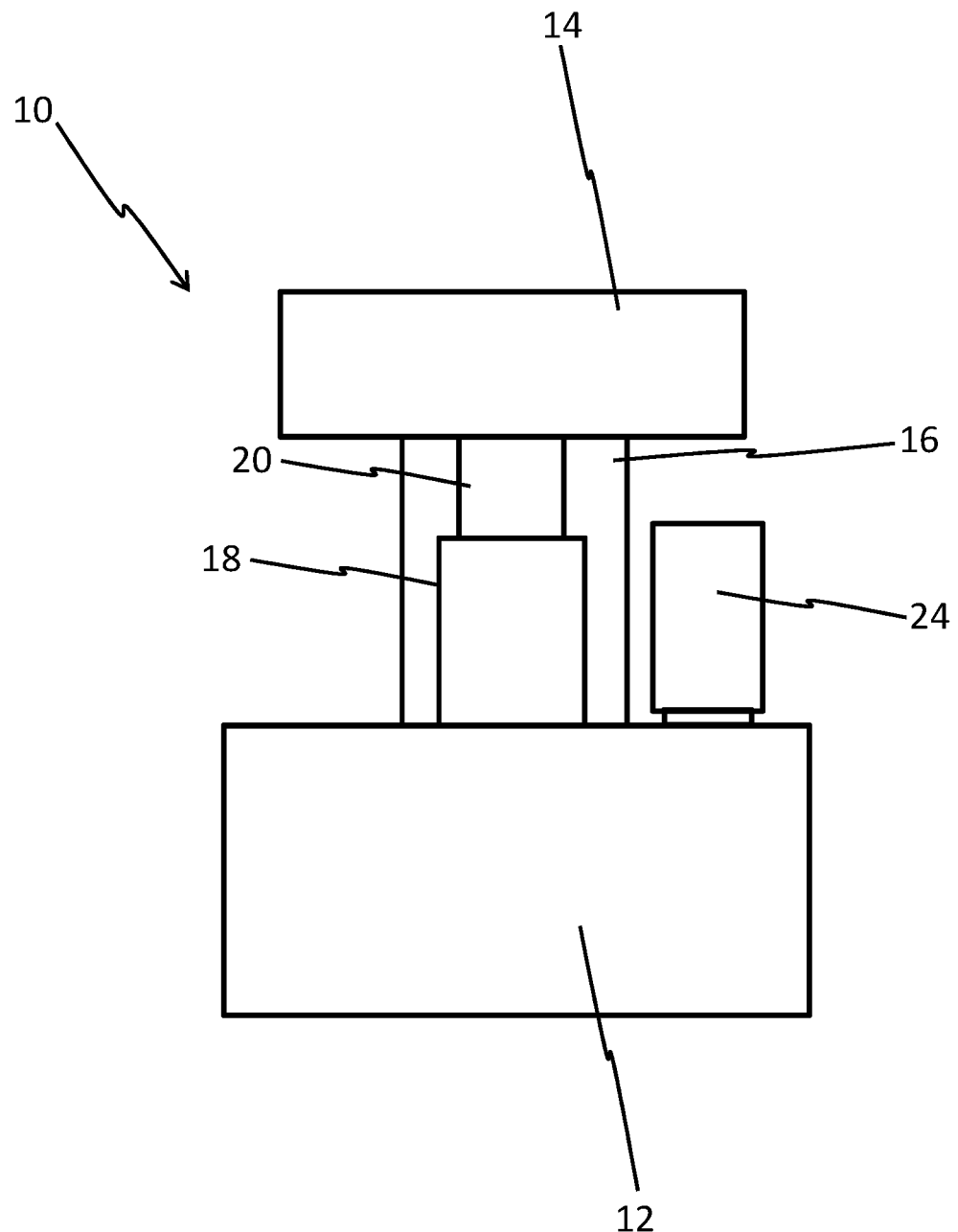
FIG. 3 shows a device according to the invention for thermal analysis in a front view t.

FIG. 3 shows a device 10 for thermal analysis according to the invention in a front view. Device 10 for thermal analysis comprises a thermoanalytical measurement device 12 and an infrared spectrometer 14, wherein the latter are connected to one another by means of a lift-swivel unit 16. Furnace 18 and coupling 20 are represented in front of lift-swivel unit 16. Furthermore, a sample changer 24 is disposed on the right beside furnace 18 and above thermoanalytical measurement device 12.

Figure 4:
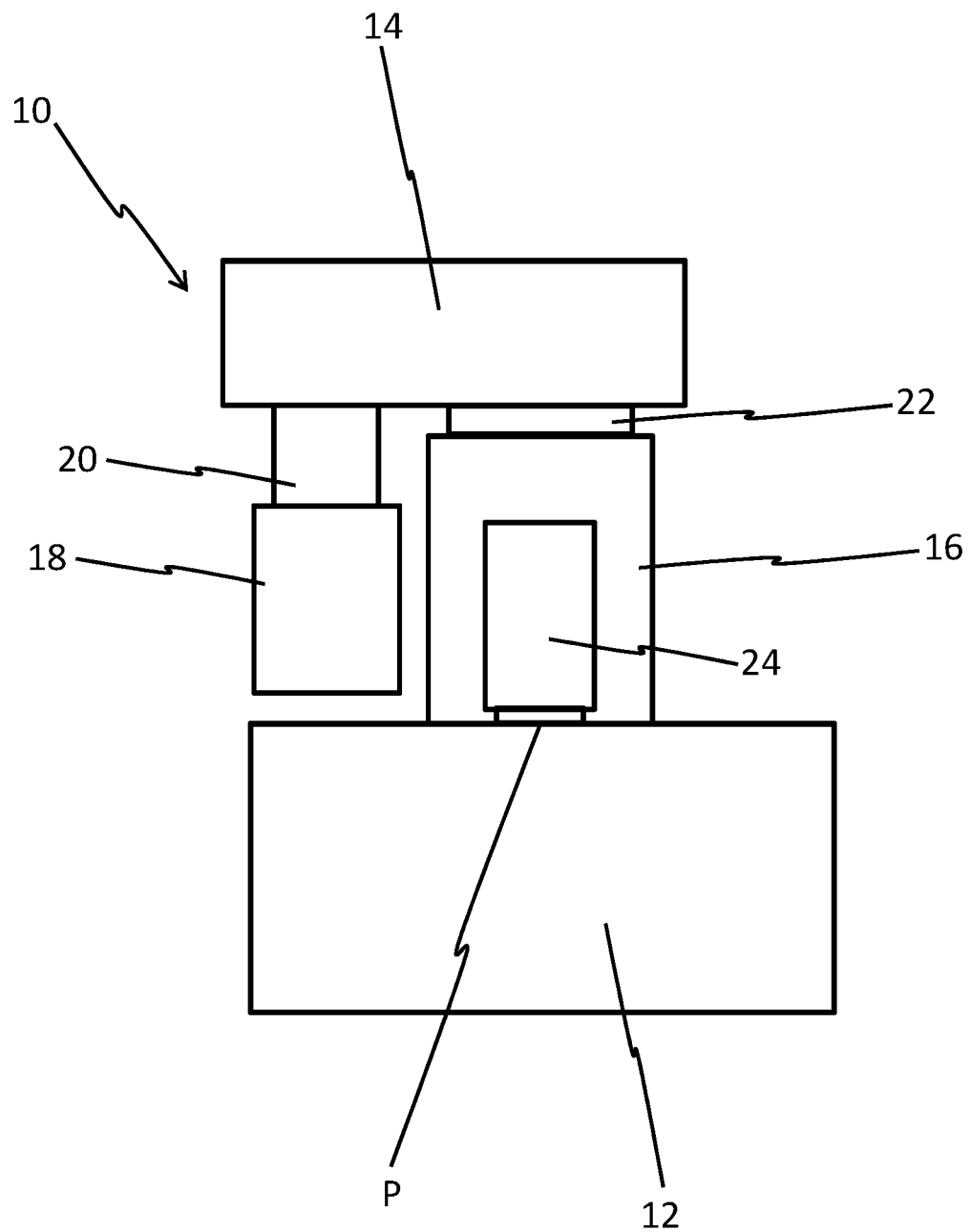
FIG. 4 shows a device according to the invention for thermal analysis, wherein the sample changer has been traversed to the position of the infrared spectrometer/furnace arrangement

FIG. 4 shows a device 10 for thermal analysis according to the invention, wherein sample changer 24 has been traversed to position P of the combination of infrared spectrometer 14 and furnace 18. In FIG. 4, the combination of infrared spectrometer 14, coupling 20 and furnace 18 has been moved away from position P of furnace 18 by means of lift-swivel unit 16. Sample changer 24 has been traversed into this position P, so that a new sample can be placed on the sample carrier (not represented). Infrared spectrometer 14, as well as furnace 18 and coupling 20, are spaced apart from thermoanalytical measurement device 12 by means of lifting device 22.

Figure 5:
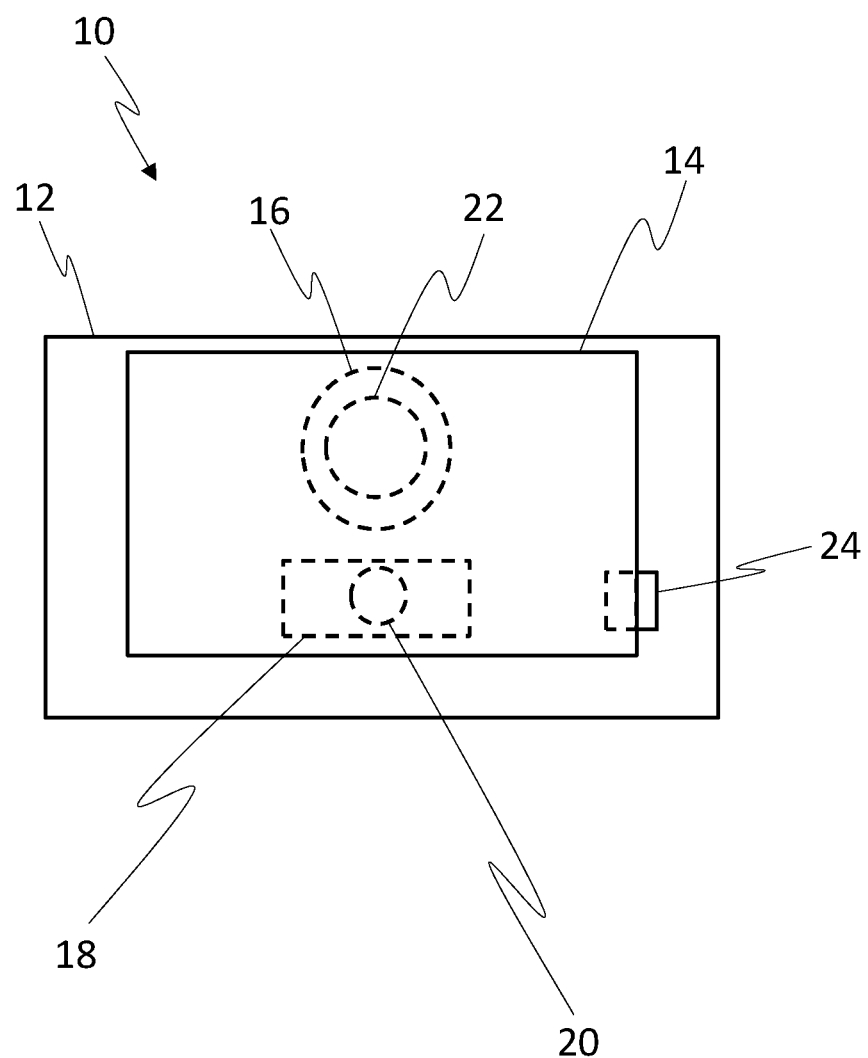
FIG. 5 shows a device according to the invention for thermal analysis in a top view.

FIG. 5 shows a device according to the invention in a top view. Device 10 for thermal analysis comprises a thermoanalytical measurement device 12 and an infrared spectrometer 14. The lift-swivel unit 16 is shown with the lifting device 22, the furnace 18 is shown with the coupling 20, and the sample changer 24 is shown as well. Some features are shown in dotted lines to reflect that they are disposed behind the infrared spectrometer as viewed from this perspective.

The invention has been described by reference to a preferred embodiment. For the person skilled in the art, however, it is conceivable for modifications or changes to the invention to be made without departing from the scope of protection of the following claims.

LIST OF REFERENCE NUMBERS 10 device for thermal analysis
12 thermoanalytical measurement device
14 infrared spectrometer
16 lift-swivel unit
18 furnace
20 coupling
22 lifting device
24 sample changer
26 sample carrier
P position of furnace on thermoanalytical measurement device

What is claimed is:

1. A device for thermal analysis, comprising:
   at least one thermoanalytical measurement device; and
   at least one infrared spectrometer;
   wherein the thermoanalytical measurement device and the at least one infrared spectrometer are connected to each other by at least one lift-swivel unit; and
   the at least one infrared spectrometer is disposed above the thermoanalytical measurement device.

2. The device for thermal analysis according to claim 1, further comprising:
   a furnace for heating a sample;
   wherein the furnace and the infrared spectrometer are connected fixedly to each other by a coupling, and the coupling is disposed between the furnace and the infrared spectrometer.

3. The device for thermal analysis according to claim 2, wherein the coupling comprises a threaded joint.

4. The device for thermal analysis according to claim 2, wherein the coupling is configured as a spacer to minimize transfer of heat from the furnace to the infrared spectrometer.

5. The device for thermal analysis according to claim 1, wherein the coupling is heated.

6. The device for thermal analysis according to claim 1, wherein the infrared spectrometer and the furnace can be raised and swiveled by the lift-swivel unit.

7. The device for thermal analysis according to claim 1, wherein the device is provided with a sample changer that can be traversed by the lift-swivel unit to a position previously occupied by the furnace.

8. The device for thermal analysis according to claim 1, wherein the lift-swivel unit is provided with at least one lifting device.

9. The device for thermal analysis according to claim 8, wherein the lifting device is a hydraulic, a mechanical or an electromechanical device.

10. The device for thermal analysis according to claim 1, wherein in addition to the infrared spectrometer, a second measurement device is disposed above the thermoanalytical measurement device, and the measurement devices are connected to the thermoanalytical measurement device by the lift-swivel unit.

11. The device for thermal analysis according to claim 1, wherein the thermoanalytical measurement device is a measurement device for differential thermal analysis or differential calorimetry, or more precisely for dynamic differential calorimetry, or for thermogravimetry, or more precisely for thermogravimetric analysis, or for simultaneous thermal analysis or for thermomechanical analysis.

12. The device for thermal analysis according to claim 1, wherein the infrared spectrometer is a measurement device for Fourier transform infrared spectroscopy and/or for near-infrared spectroscopy.

13. The device for thermal analysis according to claim 1, wherein the lift-swivel unit is fully or partially automated.

14. A device for thermal analysis, comprising:
- a thermoanalytical measurement device providing at least one of thermal analysis or differential calorimetry;
- an infrared spectrometer providing at least one of infrared or near-infrared spectroscopy;
- at least one lift-swivel unit connecting the thermoanalytical measurement device and the infrared spectrometer to each other, the infrared spectrometer being disposed above the thermoanalytical measurement device;
- a furnace configured to heat a sample; and
- a coupling detachably connecting the furnace to the infrared spectrometer such that the furnace is disposed between the infrared spectrometer and the thermoanalytical measurement device, said coupling is configured to be heated to minimize condensation in the coupling.

* * * * *